(12) United States Patent
Seiwert et al.

(10) Patent No.: US 11,518,696 B2
(45) Date of Patent: Dec. 6, 2022

(54) OZONATED WATER DELIVERY SYSTEM AND METHOD OF USE

(71) Applicant: MKS Instruments, Inc., Andover, MA (US)

(72) Inventors: Heinrich Johannes Seiwert, Berlin (DE); Christiane Le Tiec, Berlin (DE); Ulrich Alfred Brammer, Berlin (DE)

(73) Assignee: MKS Instruments, Andover, MA (US)

( * ) Notice: Subject to any disclaimer, the term of this patent is extended or adjusted under 35 U.S.C. 154(b) by 537 days.

(21) Appl. No.: 16/553,033

(22) Filed: Aug. 27, 2019

(65) Prior Publication Data

US 2020/0071208 A1 Mar. 5, 2020

Related U.S. Application Data

(60) Provisional application No. 62/724,368, filed on Aug. 29, 2018.

(51) Int. Cl.
*C02F 1/68* (2006.01)
*A61L 2/18* (2006.01)

(52) U.S. Cl.
CPC ............ *C02F 1/68* (2013.01); *A61L 2/183* (2013.01); *C02F 2201/782* (2013.01)

(58) Field of Classification Search
None
See application file for complete search history.

(56) References Cited

U.S. PATENT DOCUMENTS

| 5,261,966 | A | 11/1993 | Mashimo et al. |
| 5,425,803 | A | 6/1995 | Van Schravendijk et al. |
| 6,001,223 | A | 12/1999 | Hoffman et al. |
| 6,290,384 | B1 | 9/2001 | Pozniak et al. |
| 6,338,671 | B1 | 1/2002 | Kawashima et al. |

(Continued)

FOREIGN PATENT DOCUMENTS

| CN | 1266031 C | 7/2006 |
| CN | 101274230 A | 10/2008 |

(Continued)

OTHER PUBLICATIONS

International Search Report of PCT/US2019/048411, dated Dec. 16, 2019, 4 pages.

(Continued)

*Primary Examiner* — Richard C Gurtowski
(74) *Attorney, Agent, or Firm* — Brian F. Swienton

(57) ABSTRACT

The present application discloses a ozonated water delivery system which includes at least one contacting device in communication with at least one ultrapure water source configured to provide ultrapure water, at least one ultrapure water conduit coupled to the ultrapure water source, at least one solution in communication with the contacting device and the ultrapure water source via the ultrapure water conduit, one or more gas sources containing at least one gas in communication with at least one of the ultrapure water source, the ultrapure water conduit, and the solution conduit, at least one mixed gas conduit in communication with the at gas source and the contacting device and configured to provide at least one mixed gas to the contacting device, and at least one ozonated water output conduit may be in communication with the contacting device.

10 Claims, 9 Drawing Sheets

(56) References Cited

U.S. PATENT DOCUMENTS

| | | |
|---|---|---|
| 6,766,818 B2 | 7/2004 | Kashkoush et al. |
| 6,884,359 B2 | 4/2005 | Kambe et al. |
| 7,344,298 B2 | 3/2008 | Wilmer et al. |
| 8,038,852 B2 | 10/2011 | Tojo et al. |
| 8,430,120 B2 | 4/2013 | Laverdiere et al. |
| 9,666,435 B2 | 5/2017 | Homan et al. |
| 2002/0063345 A1* | 5/2002 | Kambe ............ B01D 61/00 261/102 |
| 2003/0158630 A1 | 8/2003 | Pham et al. |
| 2006/0021634 A1 | 2/2006 | Liu et al. |
| 2007/0043471 A1 | 2/2007 | Anderson et al. |
| 2010/0193977 A1 | 8/2010 | Yamamoto et al. |
| 2013/0079269 A1 | 3/2013 | Koike et al. |
| 2013/0313728 A1 | 11/2013 | Seiwert et al. |
| 2015/0315037 A1 | 11/2015 | Seiwert et al. |
| 2018/0133665 A1 | 5/2018 | Brammer et al. |

FOREIGN PATENT DOCUMENTS

| | | |
|---|---|---|
| CN | 101676220 B | 4/2013 |
| CN | 102640255 B | 5/2016 |
| EP | 0623381 B1 | 6/2000 |
| EP | 1512457 A1 | 3/2005 |
| EP | 0913233 B1 | 5/2005 |
| JP | 2001129376 A | 5/2001 |
| JP | 4729504 B2 | 7/2011 |
| JP | 5020784 B2 | 9/2012 |
| JP | 2010199124 A | 2/2014 |
| KR | 1020100105906 A | 9/2010 |
| TW | I402423 B | 7/2013 |
| TW | I428975 B | 3/2014 |
| TW | I445577 B | 7/2014 |
| TW | I529773 B | 4/2016 |
| WO | 2001028950 A1 | 4/2001 |
| WO | WO03/043059 A2 | 5/2003 |
| WO | WO2005/067019 A1 | 7/2005 |

OTHER PUBLICATIONS

Written Opinion of PCT/US2019/048411, dated Dec. 13, 2019, 4 pages.

* cited by examiner

OZONATED WATER DELIVERY SYSTEM AND METHOD OF USE

CROSS-REFERENCE TO RELATED APPLICATIONS

The present application claims priority to U.S. Prov. Pat. Appl. No. 62/724,368, entitled "Ozonated Water Delivery System and Method of Use," filed on Aug. 29, 2018, the entire contents of which are incorporated by reference herein.

BACKGROUND

Presently, ozone is used in numerous applications including semiconductor manufacturing, solar panel processing, sanitation applications, food processing, flat panel processing, and the like. In some applications, ozone may be dissolved in deionized water. Ozone, however, is highly reactive with deionized ultrapure water, thereby causing the ozone to decay in ultrapure water in seconds. Several applications, such as semiconductor fabrication applications, solar panel and flat panel fabrication require high ozone concentrations dissolved in ultrapure water. However, the rate of ozone decay increases as the concentration of ozone dissolved in deionized ultrapure water increases. Certain applications, for example, single semiconductor wafer processing, need dissolved ozone in randomly varying liquid flow rates, which may result in varying residence times within the supply pipes, with a higher amount of ozone decay at low liquid flow rates as an additional variance in ozone decay. In addition, ozone decay may be triggered by the presence of hydroxide-ions and peroxides normally found in trace amounts in industrially-used ultrapure water. As a consequence, ozone decay may vary between fabrication locations and/or sites due to variations in the concentration of these impurities within the ultrapure water supplied to different locations.

In response thereto, a number of techniques have been employed to control the rate of decay of ozone in ozonated water. For example, FIG. 1 shows an example of an ozonated water delivery system presently used in semiconductor fabrication applications. As shown, the ozonated water delivery system 1 includes a contacting device 3 in fluid communication with an ultrapure water source 5 (hereinafter UPW source 5) via an ultrapure water source conduit 7 (hereinafter UPW source conduit 7). A gas source and/or ozone generator 9 (hereinafter gas source 9) is in communication with the contacting device 3 via a gas inlet conduit 11. Typically, the gas mixture includes carbon dioxide ($CO_2$), ozone ($O_3$), and oxygen ($O_2$). One or more valve devices 13 and/or indicators are used to safely separate water from the gas mixture and prevent a backflow of water, gas, or both into the gas source 9. During use the gas mixture from gas source 9 is contacted within the contacting device 3 with the ultrapure water from the UPW source 5 using a countercurrent flow thereby resulting in some portion of ozone from the gas source 9 dissolving in the ultrapure water. Some carbon dioxide ($CO_2$) within the gas mixture converts into carbonic acid which lowers the concentration of the hydroxide ion. The carbonate ions scavenge hydroxyl radicals which effectively lowers the rate of decay of dissolved ozone in ultrapure water. Thereafter, the dissolved ozone is released or removed from the contacting device 3 to form a dissolved ozone output 17 via the dissolved ozone conduit 19. In addition, off gases 21, such as carbon dioxide ($CO_2$), oxygen ($O_2$), and ozone ($O_3$) may be released from the contacting device 3 via the off gas conduit 23. While the system in FIG. 1 has proven useful, a number of shortcomings have been identified. For example, the ozonated water delivery system shown in FIG. 1 permits ozone concentrations between about 25 ppm and 50 ppm. However, obtaining ozone concentrations of greater than about 50 ppm using the ozonated water delivery system 1 shown in FIG. 1 has proven difficult. Further, increases in the mass transfer efficiency would necessitate the packed column of the contacting device 3 to be higher or taller, thereby requiring a larger work area. In addition, membrane modules are commonly used for dissolving gases, such as carbon dioxide, into ultrapure water or removing residual oxygen from the ultrapure water. Unfortunately, most commercially available membrane modules include plastics such as polypropylene and/or polyethylene, or similar materials which are highly sensitive to oxidizing agents like peroxides and ozone. Further, carbon dioxide and ozone have different solubility. As such, the concentration of carbon dioxide within the contacting device varies considerably in some flow arrangements. For example, in counter flow arrangements within a packed column contacting device may result in carbon dioxide dissolving proximate to the inlet of the gas mixture conduit 11 within the contacting device 3 while ozone is dissolved proximate to the inlet of the UPW conduit 5, thereby reducing the efficiency of formation of ozonated water. FIG. 2 shows graphically the concentration profile of carbon dioxide in a packed column contacting device 3 using counter flow architecture. The abscissa in FIG. 2 represents lateral sections of the packed column forming the contacting device 3 (hereinafter column sections). The section 1 represents the top of the column proximate to the inlet of the UPW source conduit 7 and the outlet to the off gas conduit 23. The section 20 represents the bottom of the column proximate to the gas inlet conduit 11 and the dissolved ozone conduit 19.

In light of the foregoing, there is an ongoing need for an ozonated water delivery system capable of selectively providing ultrapure water having high ozone concentrations

SUMMARY

The present application discloses various embodiments of an ozonated water delivery system capable of providing higher quantities of ultrapure water having higher concentrations of dissolved ozone therein than prior art systems. In some embodiments, the ozonated water delivery system may be configured to allow for adjustment of the ozone reactivity and maintaining precise dissolved ozone measurement. More specifically, in one embodiment, the present application discloses an ozonated water delivery system, which includes at least one contacting device in communication with at least one ultrapure water source configured to provide ultrapure water. At least one ultrapure water conduit may be coupled to the ultrapure water source. Further, at least one solution may be in communication with the contacting device and the ultrapure water source via the ultrapure water conduit. One or more gas sources containing at least one gas may be in communication with at least one of the ultrapure water source, the ultrapure water conduit, and the solution conduit. During use, the gas may be used to form at least one solution when reacted with the ultrapure water. At least one mixed gas conduit may be in communication with the gas source and the contacting device. The mixed gas conduit may be configured to provide at least one mixed gas to the contacting device. Finally, at least one ozonated water output conduit may be in communication with the contacting device.

In another embodiment, the present application discloses an ozonated water delivery system which includes one or more sensors configured to measure various characteristics, concentrations, flow rates, and the like of ozonated water produced by the ozonated water delivery system. More specifically, the ozonated water delivery system may include at least one contacting device in communication with at least one ultrapure water source configured to provide ultrapure water. At least one ultrapure water conduit may be coupled to the ultrapure water source. Further, at least one solution may be in communication with the contacting device and the ultrapure water source via the ultrapure water conduit. One or more gas sources containing at least one gas may be in communication with at least one of the ultrapure water source, the ultrapure water conduit, and the solution conduit. During use, the gas may be used to form at least one solution when reacted with the ultrapure water. At least one mixed gas conduit may be in communication with the gas source and the contacting device. The mixed gas conduit may be configured to provide at least one mixed gas to the contacting device. Finally, at least one ozonated water output conduit may be in communication with the contacting device. One or more sensors may be positioned within the ozonated water delivery system and used to measure a variety of characteristics of the output ozonated water, such as ozone concentration, flow rate, temperature, and the like.

In another embodiment, the present application discloses an ozonated water delivery system which includes multiple contacting devices therein. More specifically, the present application discloses an ozonated water delivery system having a first contacting device and at least a second contacting device therein. At least one ultrapure water source may be configured to provide ultrapure water to the first contacting device. At least one ultrapure water conduit may be coupled to the ultrapure water source and the first contacting device. At least one solution conduit may be in communication with the first contacting device and the ultrapure water source via the ultrapure water conduit. At least one gas source containing at least one gas may be in communication with at least one of the ultrapure water source, the ultrapure water conduit, and the solution conduit. During use, the gas may be used to form at least one solution when reacted with the ultrapure water. The second contacting device is in communication with the first contacting device via at least one first contacting device conduit configured to transport ozonated water outputted from the first contacting device to the second contacting device. At least one mixed gas conduit may be in communication with the gas source and the second contacting device. The mixed gas conduit may be configured to provide at least one mixed gas to the second contacting device. At least one off gas conduit is in communication with the second contacting device and the first contacting device, wherein the off gas conduit is configured to direct a portion of the mixed gas from the second contacting device to the first contacting device. At least one ozonated water output conduit may be in communication with the second contacting device.

The present application also discloses a method of providing ozonated water. More specifically, the present application discloses a method of providing ultrapure water having higher concentrations of dissolved ozone at higher quantities than presently available. In one embodiment, the method of providing ozonated water includes forming an aqueous carbon dioxide solution comprised of carbon dioxide dissolved in ultrapure water. Flowing the aqueous carbon dioxide solution into at least one contacting device. Flowing at least one mixed gas having at least a portion of which comprises ozone into the contacting device having the aqueous carbon dioxide solution flowing therein. Dissolving at least a portion of the ozone within the ultrapure water within the contacting device. Delaying the rate of ozone decay of the dissolved ozone within the ultrapure water with the carbon dioxide constituent of the aqueous carbon dioxide solution, and outputting ozonated water from the contacting device.

In another embodiment, the present application also discloses a method to adjust or regulate the ozone reactivity. More specifically, the present application discloses a method of measuring the ozone reactivity and control the amount of carbon dioxide gas flowing into the first contacting device in response thereto. In one embodiment, the second sensor may be used to selectively regulate the flow conditions through at least one valve within the ozonated water delivery system Other features and advantages of the novel ozonated water delivery system discloses herein will become more apparent following a consideration of the following detailed description.

BRIEF DESCRIPTION OF THE DRAWINGS

The novel aspects of the ozonated water delivery system and method of use as described herein will be more apparent by review of the following figures, wherein.

DETAILED DESCRIPTION

Figure 1:
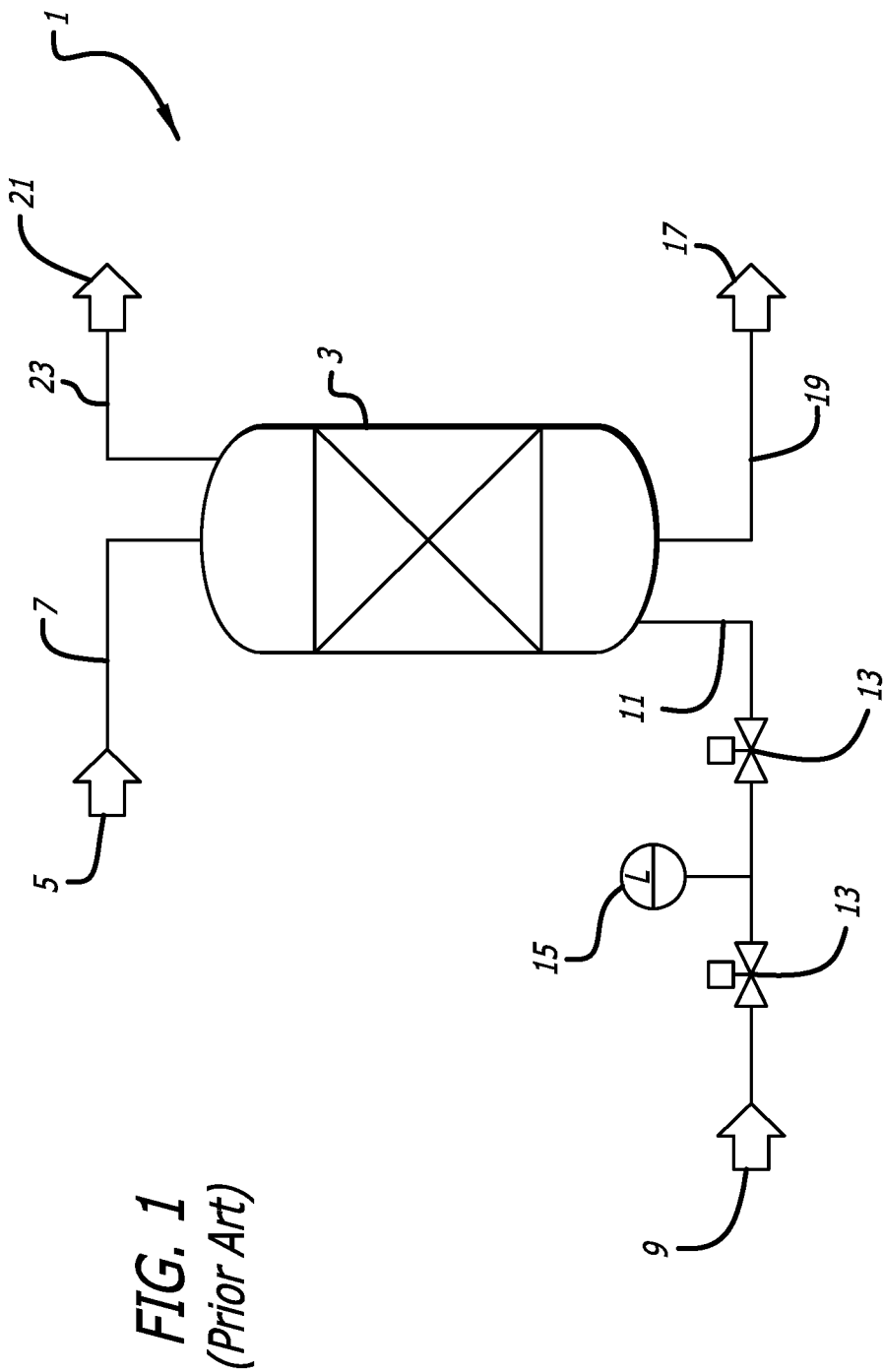
FIG. 1 shows a schematic diagram of a prior art ozonated water delivery system.
Figure 2:
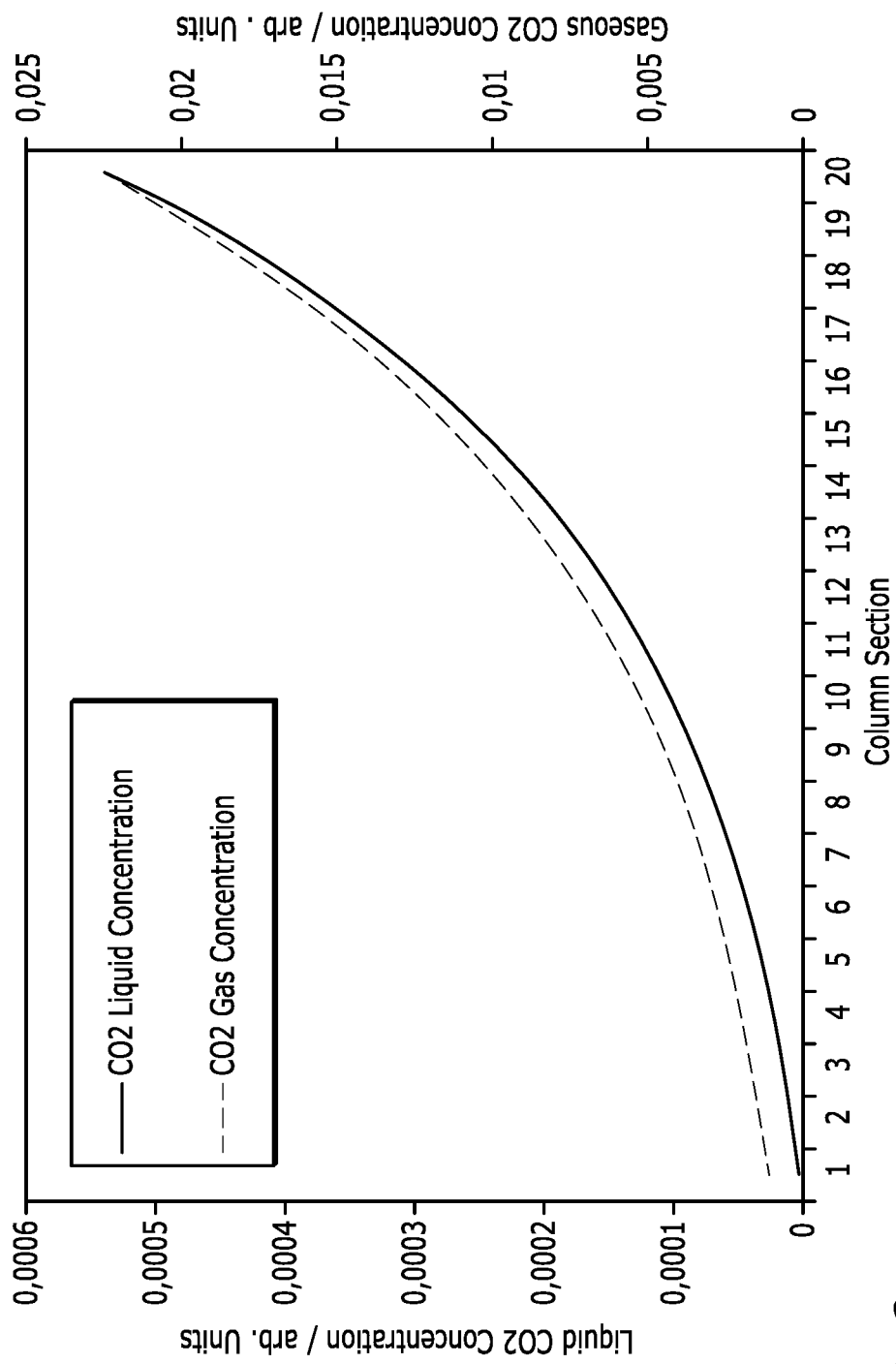
FIG. 2 shows a graph depicting the concentration profile of carbon dioxide in the prior art packed column contacting device shown in FIG. 1.

The present application discloses several embodiments of a novel ozonated water delivery system. In one embodiment, the novel ozonated water delivery system disclosed herein may be configured to provide ozonated water having ozone concentrations of greater than about 50 ppm. In another embodiment, the novel ozonated water delivery system disclosed herein may be configured to provide ozonated water having ozone concentrations of greater than about 100 ppm Optionally, the novel ozonated water delivery system disclosed herein may be configured to provide ozonated water having ozone concentrations of about 50 ppm or less. Further, the novel ozonated water delivery systems may be configured to provide ozonated water having ozone concentrations of greater than about 50 ppm with flow rates of ultrapure water of 20 liter per minute (LPM) or greater, although those skilled in the art will appreciate that the ozonated water delivery system disclosed herein may be configured to provide ultrapure water at flow rates of less than about 20 LPM. In another embodiment, the ozonated water delivery systems may be configured to provide ozonated water having ozone concentrations of greater than about 100 ppm at ultrapure water flow rates of 20 LPM or greater. Optionally, the ozonated water delivery systems may be configured to provide ozonated water having any variety of ozone concentrations at ultrapure water flow rates of 2 LPM or greater. The system can be optionally configured to provide a constant ozone concentration at randomly varying ozonated water flow rates between 2 LPM and more than 20 LPM.

FIGS. 3-6 show schematic diagrams of various embodiments of a novel ozonated water delivery system. As shown, the ozonated water delivery system 30 disclosed herein includes at least one contacting device 32. In the illustrated embodiments, a single contacting device 32 is used in the ozonated water delivery system 30 although those skilled in the art will appreciate that any number of contacting devices may be used. Further, in one embodiment the contacting device 32 comprises a packed column architecture. Further, in one embodiment the contacting device 32 comprises a packed column filled with tower packing. In another embodiment, the contacting device 32 comprises a membrane-based device or at least one membrane module. The contacting device 32 may be in fluid communication with at least one deionized ultrapure water source 34 (hereinafter UPW source 34) via at least one ultrapure water conduit 36 (hereinafter UPW conduit 36), the UPW conduit 36 configured to transport deionized ultrapure water from the UPW source 34 to the contacting device 32. In the illustrated embodiments, at least one ultrapure water and/or reactant inlet 40 may be formed on a surface of the contacting device 32. Those skilled in the art will appreciate than any number of inlets or outlet may be formed on the contacting device 32. Although not shown in FIGS. 3 and 4, those skilled in the art will appreciate that one or more controllers, valve devices, flow restrictors, sensors, indicators, flow controllers, and the like may be included on the UPW conduit 36.

Referring again to FIGS. 3-6, at least one gas or fluid source 60 configured to provide one or more types of gases, reactant, and/or fluids (hereinafter gas source 60) may be in communication with at least one of the UPW source 34, the UPW conduit 36, and/or the contacting device 32. In the illustrated embodiment, the gas source 60 is coupled to at least one gas conduit 42 which is coupled to the UPW conduit 36 via at least one coupling member 48. As such, the ultrapure water flowing through the UPW conduit 36 may react with at least one gas or fluid within the gas conduit 42 to form at least one reacting solution, which may flow into the contacting device 32 via the at least one ultrapure water inlet 40. For example, the deionized ultrapure water may be reacted with carbon dioxide to produce an aqueous carbon dioxide solution. Further, like the UPW conduit 36, the gas conduit 42 may include one or more controllers, valve devices, restrictors, mass flow controllers, sensors, indicators, flow regulators and the like thereon or in communication therewith. For example, in the embodiments shown in FIGS. 3, 4, and 6, the gas conduit 42 includes two (2) valves 44 and one (1) indicator 46 configured to prevent the backflow of water and or gas into gas source, although those skilled in the art will appreciate that any variety of components may be used on the gas conduit 42 for any variety of applications. Optionally, FIG. 5 shows an alternate embodiment of an ozonated water delivery device 30. As shown, the ozonated water delivery device 30 shown in FIG. 5 includes many of the components of the ozonated water delivery device 30 shown in FIGS. 3, 4, and 6. However, the ozonated water delivery device 30 shown in FIG. 5 includes a valve 44 positioned on at least one of the UPW conduit 36, solution conduit 38, or both. Further, at least one (1) valve 44, at least one (1) flow restrictor 50, and at least one (1) check valve 52, and at least one control valve 54 may be positioned on the gas conduit 42. In the illustrated embodiment, the carbon dioxide is added to the ultrapure water flowing within the UPW conduit 36 upstream of the control valve 54.

In one embodiment, the gas source 60 may be configured to deliver carbon dioxide (CO2) to the ultrapure water flowing within the ultrapure conduit 36 to form an aqueous carbon dioxide solution prior to the ultrapure water entering the contacting device 32 via at least one solution conduit 38. During use, the carbon dioxide constituent of the aqueous carbon dioxide solution may be used to reduce the rate of decay of dissolved ozone within contacting device 32 during use. For example, in one embodiment, the gas source 60 and gas conduit 42 are configured to provide a flow of carbon dioxide to the ultrapure water flowing within the UPW conduit 36 at a flow rate of about 0.01 standard liters per minute (hereinafter SLPM) to about 0.5 SLPM. Optionally, the gas source 60 and gas conduit 42 are configured to provide a flow of carbon dioxide to the ultrapure water flowing within the UPW conduit 36 at a flow rate of about 0.005 standard liters per minute (hereinafter SLPM) to 3.0 SLPM or more. In one embodiment, the gas source 60 may be configured to provide a constant flow of gas (e.g. carbon dioxide, etc.) to the UPW conduit 36 at a fixed flow rate, irrespective of the flow rate of the ultrapure water flowing into the contacting device 32. As such, the effective content of carbon dioxide in the ultrapure water may be higher at lower ultrapure water flow rates, thereby resulting in a higher concentration of dissolved ozone in the ultrapure water. In another embodiment, the gas source 60 may be configured to provide a flow of gas (e.g. carbon dioxide, etc.) to the UPW conduit 36 at a fixed ratio of ultrapure water to gas. In another embodiment, the gas source 60 and gas conduit 42 are configured to provide a flow of carbon dioxide to the ultrapure water flowing within the UPW conduit 36 at a flow rate of about 0.05 SLPM to about 0.3 SLPM. Optionally, the gas source 60 and gas conduit 42 are configured to provide a flow of carbon dioxide to the ultrapure water flowing within the UPW conduit 36 at a flow rate of about 0.1 SLPM to about 0.2 SLPM, although those skilled in the art will appreciate that the gas source 60 and gas conduit 42 may be configured to provide a flow of carbon dioxide to the ultrapure water flowing within the UPW conduit 36 at any desired flow rate. As such, one or more mass flow controllers 44 and valves 46 may be used to selectively control the rate of the introduction of carbon dioxide to the UPW conduit 36. In an alternate embodiment, the gas source 60 may be configured to provide nitrogen to the gas conduit 42. Optionally, the gas source 60 may be configured to provide any variety of gases or fluids to at least one of the gas conduit 42, the UPW source 34, contacting device 32, and the like.

As shown FIGS. 3-6, the gas source 60 may be in communication with the contacting device 32 via at least one mixed gas conduit 62 and at least one mixed gas inlet 68. In the illustrated embodiments, a single gas source 60 is in fluid communication with the contacting device 32. For example, the single gas source 60 shown in FIGS. 3-6 may be configured to provide a mixed gas consisting of oxygen ($O_2$), ozone ($O_3$), and carbon dioxide ($CO_2$) to the contacting device 32. In another embodiment the mixed gas consists of oxygen ($O_2$), ozone ($O_3$), carbon dioxide ($CO_2$), and less than about 2 ppm nitrogen ($N_2$), although those skilled in the art will appreciate that more than about 2 ppm nitrogen ($N_2$) may be used. Other gases include, without limitations, nitrogen, nitrogen dioxide, dinitrogen oxide. In an alternate embodiment, multiple gas sources 60 may be coupled to or otherwise in fluid communication with the contacting device 32. For example, individual sources of ozone ($O_3$)/oxygen ($O_2$), and carbon dioxide ($CO_2$) may each be coupled to the gas conduit 62 such that the mixed gas conduit 62 mixes and transports the mixed gas from the individual sources to the contacting device 32. In one embodiment, the gas source 60 may be in communication with and/or may include at least one ozone generator configured to provide ozone to the mixed gas conduit 62. During use, the carbon dioxide introduced into the contacting device 32 within the mixed gas via the mixed gas conduit 62 has the function to increase the efficiency of the ozone generation in the ozone generator as part of the mixed gas source 60 and inhibits the ozone decay of the ozone dissolved within the water at the mixed gas input area within the contacting device 32, while the carbon dioxide constituent of the aqueous carbon dioxide solution reduces the rate of decay of the dissolved ozone at the gas outlet side of the contacting device 32. As such, any variety of additional gases (e.g. carbon dioxide, nitrogen, nitrogen dioxide, dinitrogen oxide, and the like) may be used to improve and/or selectively control the efficiency of the process of converting oxygen to ozone within in ozone generator.

As shown in FIGS. 3-6, at least one valve, mass flow controller, indicator, sensor, and the like may be positioned on or in communication with at least one of the gas source 60, the mixed gas conduit 62, or both. For example, two (2) valves 64 and one (1) indicator 66 are included in the embodiments of the ozonated water delivery system 30 shown in FIGS. 3-6, although those skilled in the art will appreciate that any number or valves, mass flow controllers, indicators, sensors, and the like may be coupled to or in communication with the mixed gas conduit 62.

Referring again to FIGS. 3-6, during use, the aqueous carbon dioxide solution is introduced into the contacting device 32 via the solution conduit 38. As stated above, the mixed gas from the mixed gas conduit 62 is introduced into the contacting device 32. Ozone within the mixed gas reacts with and dissolves within the ultrapure water to form dissolved ozone ($DIO_3$). The carbon dioxide within the ultrapure water introduced into the contacting device 32 via the solution conduit 38 may be used to inhibit the rate of decay of the newly formed dissolved ozone. Thereafter, the ozonated water is released at the ozonated water output 70 from the contacting device 32 via at least one ozonated water conduit 72. In one embodiment, the flow rate of ozonated water from the ozonated water output 70 is from about 0.2 LPM to about 70 LPM. In another embodiment, the flow rate of ozonated water from the ozonated water output 70 is from about 3 LPM to about 40 LPM. Optionally, the ozonated water delivery system 30 shown in FIGS. 3 and 4 may be configured to output about 2 LPM to about 20 LPM of ozonated water from the ozonated water output 70. Further, off gases 80, such as oxygen ($O_2$), ozone ($O_3$), carbon dioxide ($CO_2$), and other gases may be removed from the contacting device 32 via at least one off gas conduit 82.

Figure 3:
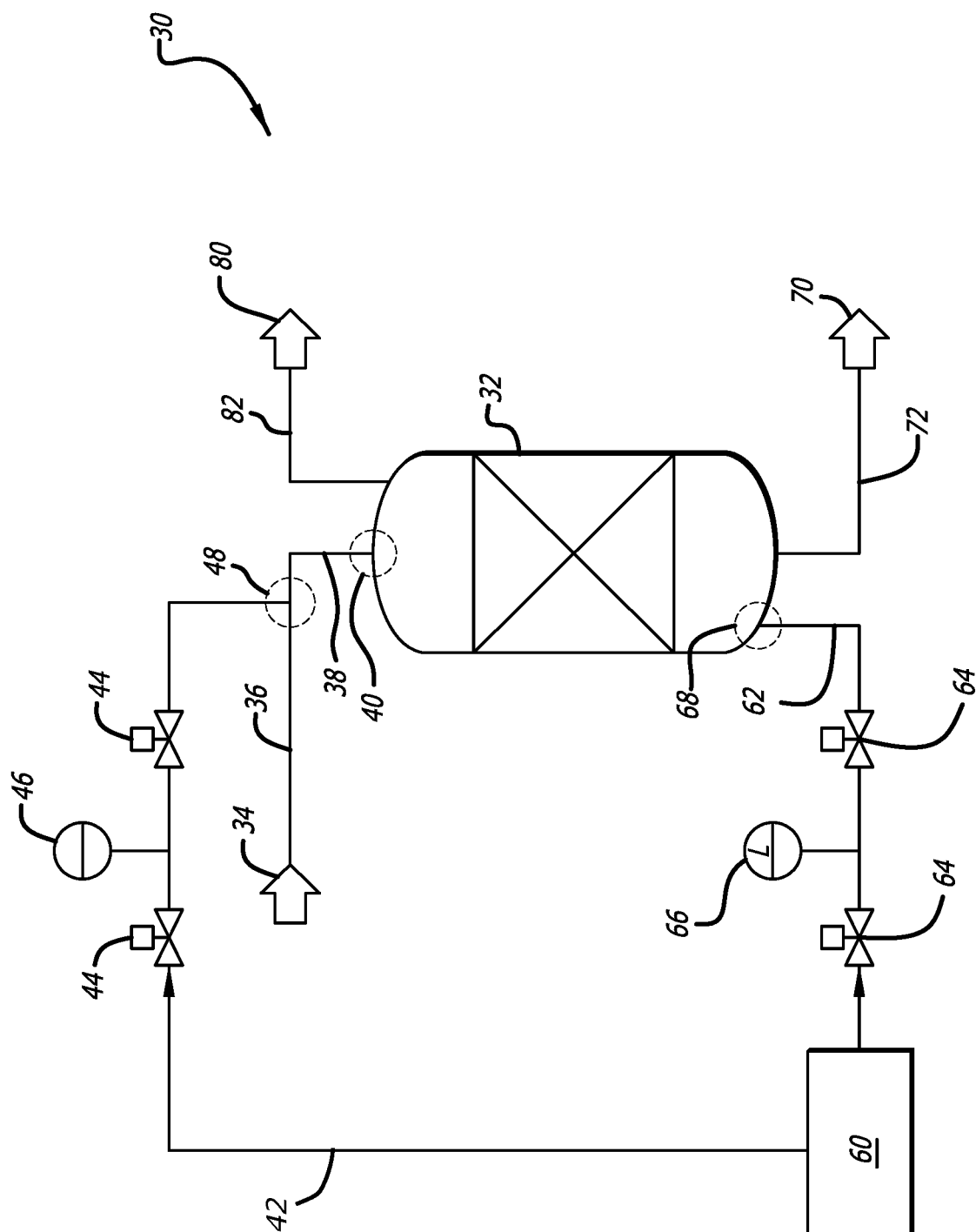
FIG. 3 shows a schematic diagram of an embodiment of a ozonated water delivery system having a gas source providing gaseous carbon dioxide to the ultrapure water used in the contacting device.
Figure 4:
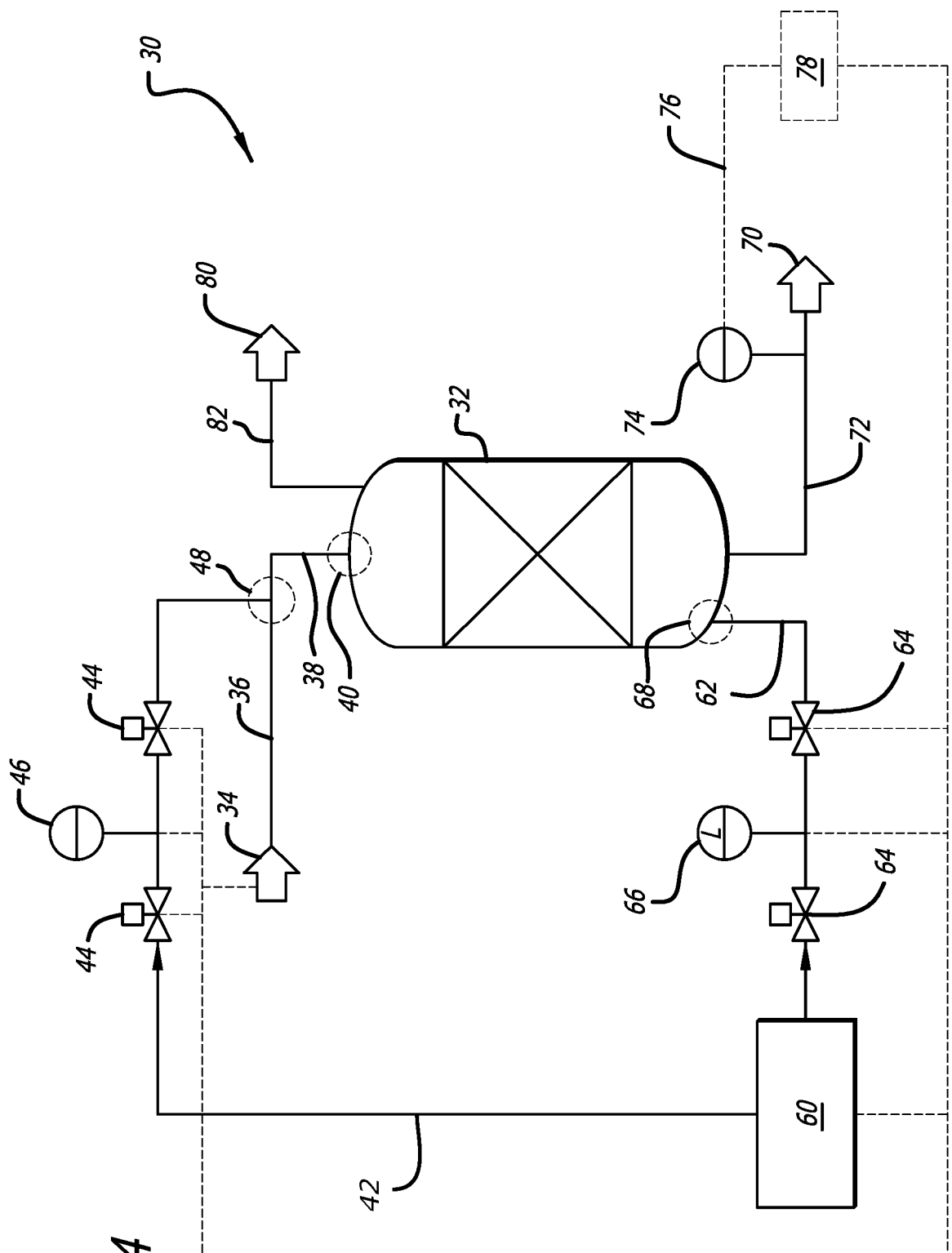
FIG. 4 shows a schematic diagram of another embodiment of an ozonated water delivery system having a gas source providing gaseous carbon dioxide to the ultrapure water used in the contacting device.
Figure 5:
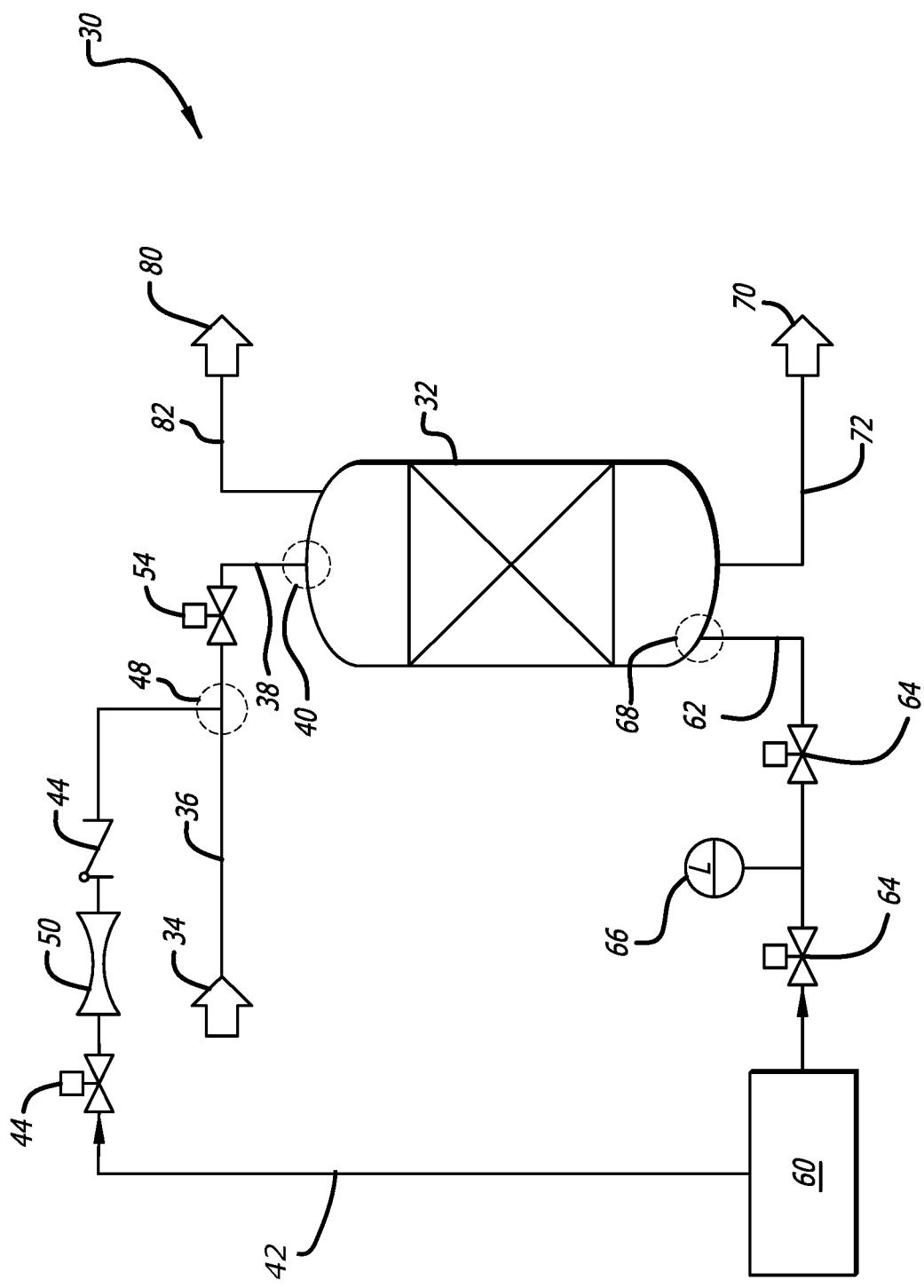
FIG. 5 shows a schematic diagram of another embodiment of an ozonated water delivery system having a gas source providing gaseous carbon dioxide to the ultrapure water used in the contacting device.
Figure 6:
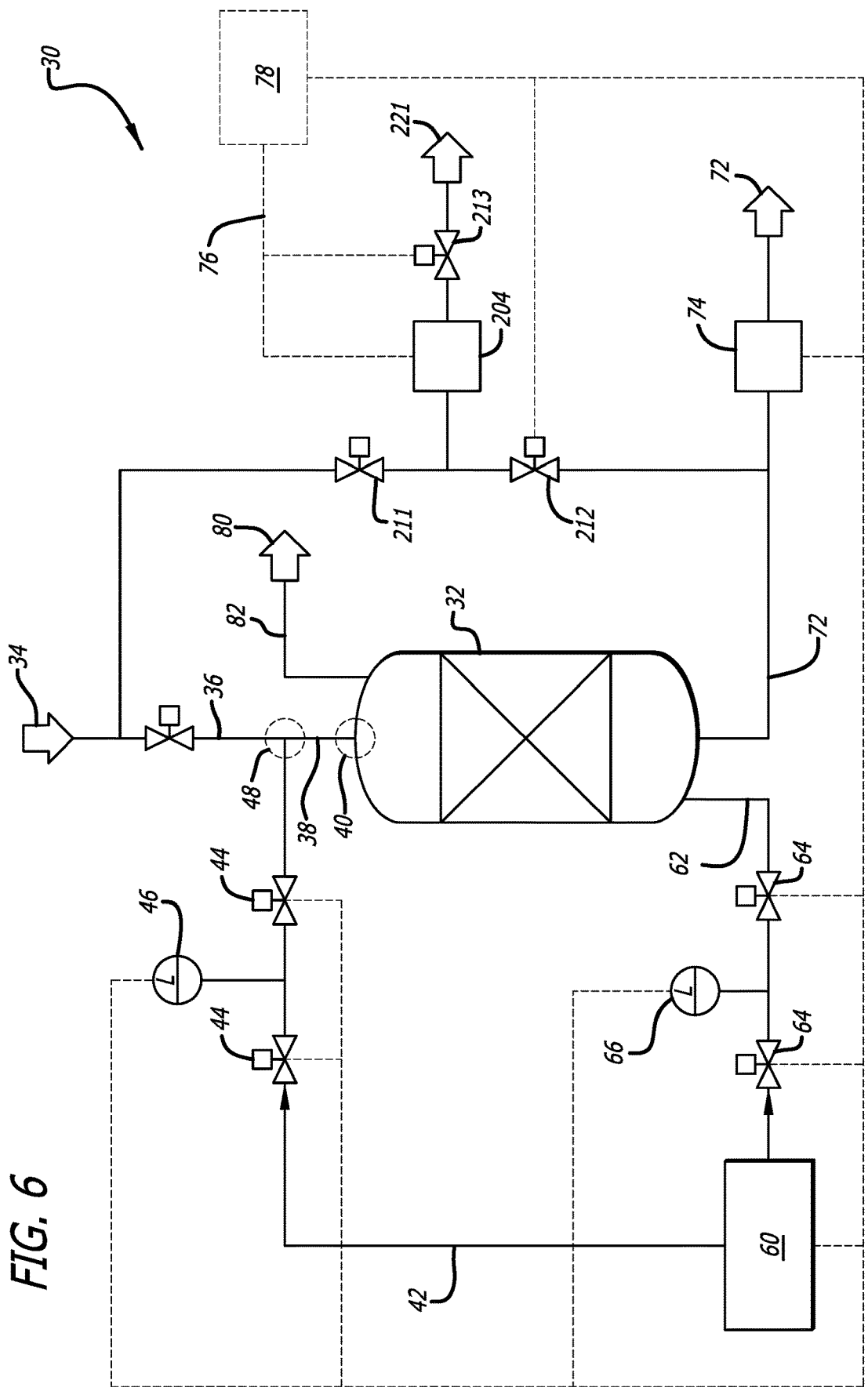
FIG. 6 shows a schematic diagram of another embodiment of an ozonated water delivery system incorporating a device for measuring the ozone reactivity.
Figure 7:
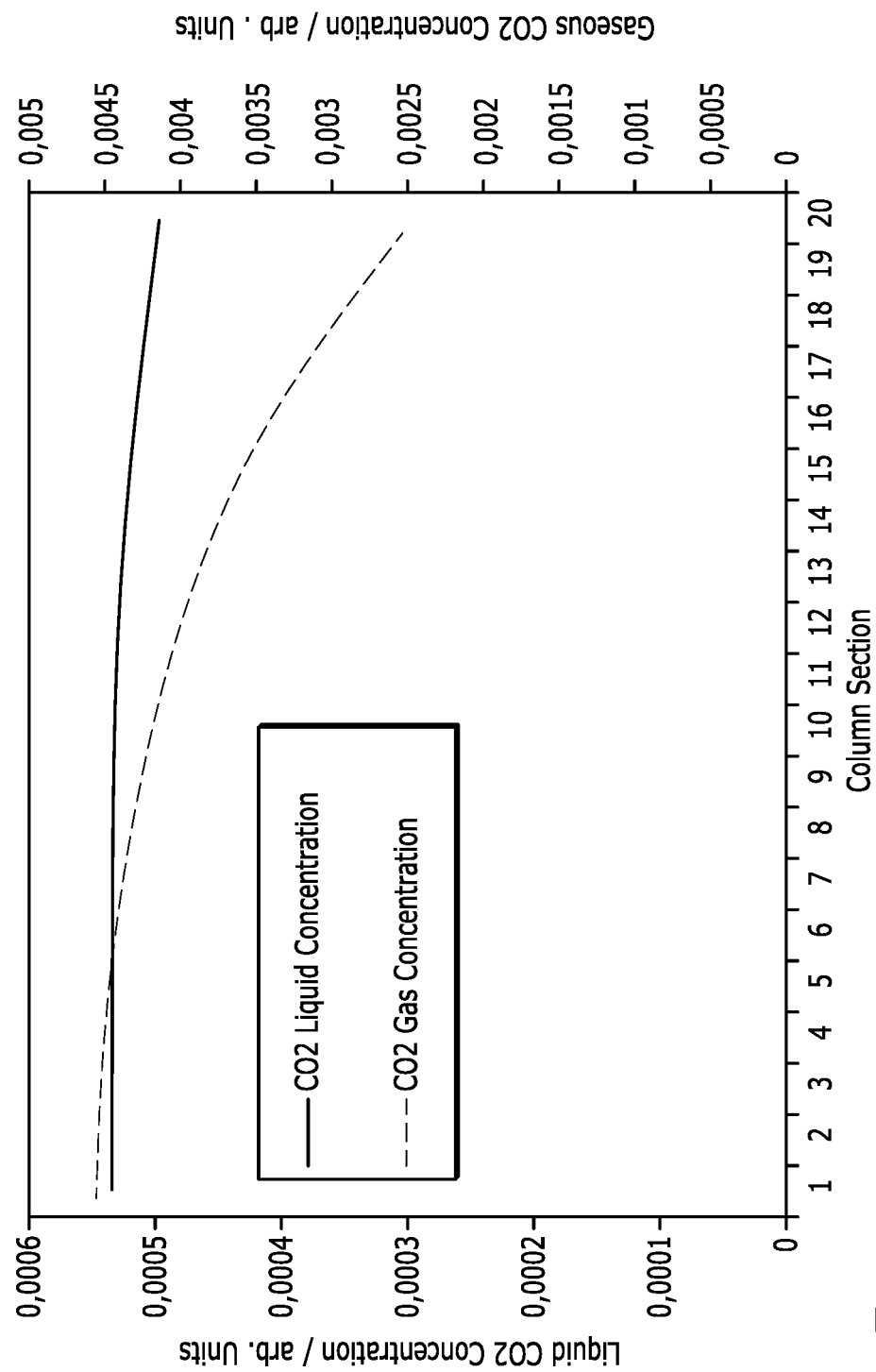
FIG. 7 shows a graph depicting the concentration profile of carbon dioxide in the contacting device shown in FIGS. 3 and 4.

FIGS. 4 and 6 shows alternate embodiments of the ozonated water delivery system 30 shown in FIG. 3 having at least on processor therein. As shown, at least one sensor, indicator, valve or the like may be positioned on the ozonated water conduit 72. For example, in the illustrated embodiment, a sensor 74 is coupled to the ozonated water conduit 72 although those skilled in the art will appreciate that any variety of other components may similarly be included. For example, in one embodiment the sensor 74 may be configured to measure ozone concentrations proximate to the ozonated water conduit 72, although those skilled in the art will appreciate that the various ozonated water delivery systems disclosed herein may include one more sensors 74 positioned at various locations within the ozonated water delivery system, the sensors 74 configured to measure ozone concentration, carbon dioxide concentration, flow rates, temperature, and the like. The sensor 74 may be in communication with at least one processor 78 via at least one processor conduit 76. Further, the processor 78 may be in communication with at least one of the UPW source 34, valve 44, indicator 46, gas source 60, valve 64, and indicator 66 via the processor conduit 76. As such, the processor 78 may be configured to receive data from and provide data to at least one of the UPW source 34, valve 44, indicator 46, gas source 60, mass flow controller 64, indicator 66, and sensor 74. As such, the processor 78 may be configured to permit, restrict, and/or otherwise control the flow of ultrapure water, mixed gas, and/or ozonated water within the system via sensors, UPW sources, valves, mass flow controllers, gas sources, and the like used throughout the system. During use, the processor 78 may be configured to monitor the ozone concentration, water flow rate, and similar characteristics of the ozonated water and operational characteristics such as pressure within the contacting device 32, the pressure within the UPW source 34, and the like. Further, the processor 78 may be configured to selectively vary the performance of the UPW source 34, mass valve 44, indicator 46, gas source 60, valve 64, indicator 66, and sensor 74 accordingly. The pressure in the contacting device 32 may be controlled by the processor 78 to an effectively constant value. The pressure of the contacting device 32 may be configured to be between 1 bar and 4 bar, such as between 1.8 bar and 2.5 bar, although those skilled in the art will appreciate that the pressure within the contacting device 32 may be higher or lower depending on the application. FIG. 7 shows graphically the $CO_2$ liquid concentration and $CO_2$ gas concentration profile using the architecture shown in FIGS. 3 and 4. Those skilled in the art will appreciate that the embodiments shown in FIGS. 5 and 6 would generate a similar graphically representation of $CO_2$ liquid concentrations and $CO_2$ gas concentration. As shown, the distribution of $CO_2$ within the contacting device 32 is more uniform than the concentration profile of carbon dioxide in a packed column contacting device 3 using the prior art counter flow architecture shown in FIG. 1. Further, those skilled in the art will appreciate that architectures which include a membrane contacting device suffer a similar non-uniformity in the concentration profile of carbon dioxide like the concentration profile of carbon dioxide in a packed column contacting device 3 using the prior art counter flow architecture shown in FIG. 1, due to the principle similarity of the transport processes.

FIG. 6 shows an embodiment of an ozonated water delivery system which includes two ozone sensors, although those skilled in the art will appreciate that any number of sensors may be used. In one embodiment, the first sensor 74 may be configured to operate continuously and may, in cooperation with the controllable valve 212 and processor 78, control the ozone concentration in the outputted ozonated water 72. Optionally, in the illustrated embodiment, the ozonated water delivery system 30 may include at least a second sensor 204 (e.g. ozone measurement device). In one embodiment, the second sensor 204 may be configured to control the accuracy of the measurement device 74. In another embodiment, the second sensor 204 may be configured to measure any variety of characteristics of an output of the ozonated water delivery system 30. For example, the second sensor 204 may be configured measure the dissolved ozone concentration in the conduit 72, and, in cooperation with the processor 78, compare the measured ozone concentration measure by the first sensor 74 to ozone concentration measured by the second sensor 204, and when there is a deviation, adjust the zero point of the first sensor 74 accordingly. In one embodiment, at least one valve 213 may be used to selectively control the flow condition within the system, for example, after filling the ozone sensor 204 with fresh ozonated water. Optionally, the ozone concentration of the water staying stagnant in the sensor 204 will then be followed over time by the controller 78. The decay rate may be calculated from the ozone concentration curve over time. Thereafter, the amount of carbon dioxide supplied may be controlled by a controller 78 based on the measured ozone decay rate, in order to achieve the desired ozone reactivity at the treated target surface. In one embodiment, one or more ozone sensors 204 (optical sensors, visible light sensors, IR sensors, UV sensors, and the like) may be used. For example, the ozone sensor 204 may be configured to measure ozone based on visible light absorption. The second sensor 204 may be configured to operate as a reference sensor, configured to measure the ozone concentration at a given time in the supplied water. The measurement values of both sensors may then compared. As such, this arrangement allows for continuous operation of the first sensor 74 without interruptions due to filling the sensor with water without dissolved ozone for recalibration of the zero point, which is economically advantageous for the whole system, due to a higher amount of uptime.

Figure 8:
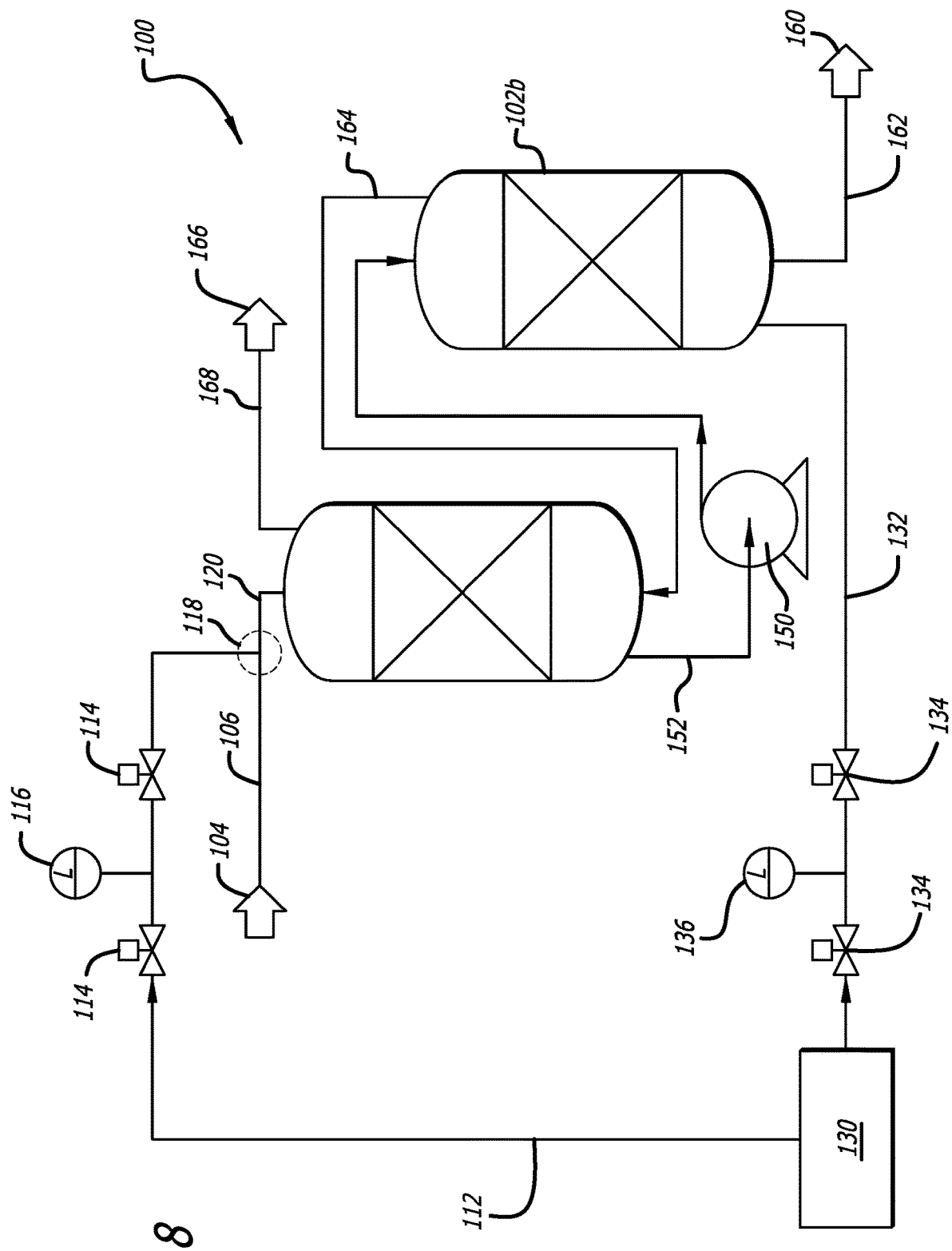
FIG. 8 shows a schematic diagram of an embodiment of an ozonated water delivery system incorporating multiple contacting devices.
Figure 9:
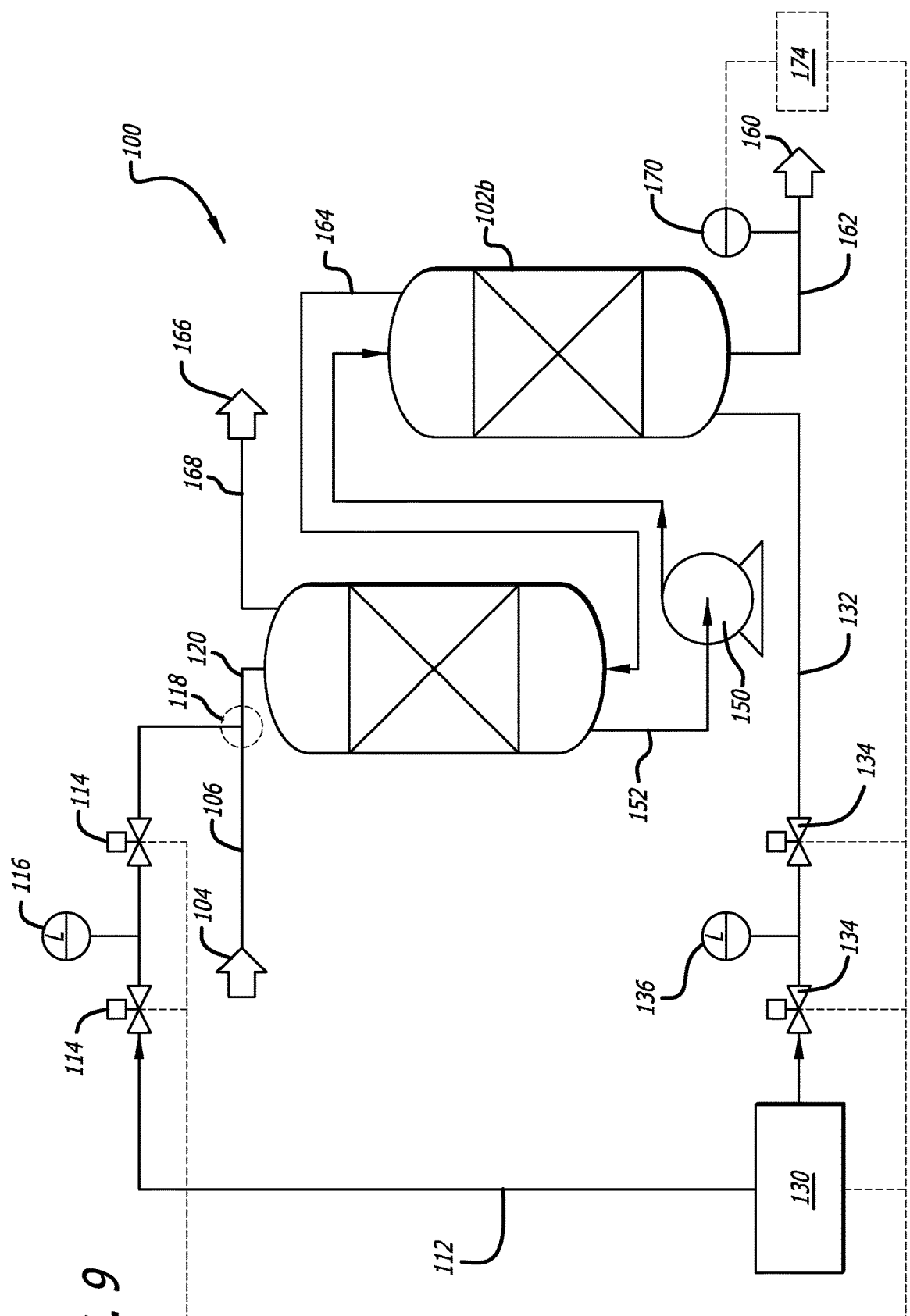
FIG. 9 shows a schematic diagram of another embodiment of an ozonated water delivery system incorporating multiple contacting devices.

FIGS. 8 and 9 show another embodiment of an ozonated water delivery system. As shown, the ozonated water delivery system 100 includes a first contacting device 102a and at least a second contacting device 102b. In one embodiment, the first contacting device 102a, second contacting device 102b, or both comprise a packed column architecture. Optionally, at least one of the first contacting device 102a and/or second contacting device 102b need not comprise a packed column architecture. For example, at least one the first contacting device 102a and/or second contacting device 102b may comprise a membrane-based device or at least one membrane module. The first contacting device 102a may be in fluid communication with at least one ultrapure water source 104 (hereinafter UPW 104) via at least one ultrapure water conduit 106 (hereinafter UPW conduit 106). Again, although not shown in FIGS. 8 and 9, those skilled in the art will appreciate that one or more controllers, valve devices, sensors, indicators, and the like may be included on the coupling member 106.

Referring again to FIGS. 8 and 9, at least one gas source 130 may be in communication with at least one of the UPW source 104, the UPW conduit 106, and/or the contacting device 102a via at least one gas conduit 112. In the illustrated embodiment, the gas source 130 is coupled at least one gas conduit 112 which is coupled to the UPW conduit 106 via at least one coupling member 118. Like the previous embodiment, the ultrapure water flowing through the UPW conduit 106 reacts with the gas within the gas conduit 112 to form at least one reacting solution. Further, like the UPW conduit 106, the gas conduit 112 may include one or more controllers, valve devices, mass flow controllers, sensors, indicators, and the like thereon or in communication therewith. For example, in the illustrated embodiment the gas conduit 112 includes two (2) valves 114 and one (1) indicator 116 thereon configured to prevent the backflow of water and/or gas into the gas source 130; although those skilled in the art will appreciate that any number of valves, indicators, controllers, and the like may be included on or in communication with the gas conduit 112 for any variety of applications.

Optionally, the gas source 130 may be configured to deliver carbon dioxide (CO2) to the ultrapure water flowing within the ultrapure conduit 106 to form an aqueous carbon dioxide solution prior to the ultrapure water entering the first contacting device 102a via at least one solution conduit 120. Those skilled in the art will appreciate that the gas source 130 and gas conduit 112 may be configured to provide a flow of carbon dioxide to the ultrapure water flowing within the UPW conduit 106 at any desired flow rate. For example, in one embodiment, the gas source 130 and gas conduit 112 may be configured to provide a flow of carbon dioxide to the ultrapure water flowing within the UPW conduit 106 at a constant flow rate, independent of the flow rate of ultrapure water.

Referring again to FIGS. 8 and 9, the gas source 130 may in communication with the second contacting device 102b via at least one mixed gas conduit 132. Like the previous embodiment, the gas source 130 may be coupled to, in communication with, or include therein at least one ozone generator. In the illustrated embodiment, a single gas source 130 is in fluid communication with the second contacting device 102b, although any number of gas sources 130 may be used. Like the previous embodiment, the gas source 130 shown in FIGS. 7 and 8 may be configured to provide a mixed gas consisting of oxygen (O2), ozone (O3), and carbon dioxide (CO2) to the contacting device 32. In an alternate embodiment, multiple gas sources 130 may be coupled to or otherwise in fluid communication with the second contacting device 102b. For example, individual sources of oxygen (O2), ozone (O3), and carbon dioxide (CO2) may each be coupled to the mixed gas conduit 132 such that the mixed gas conduit 132 mixes and transports the mixed gas from the individual sources to the second contacting device 102b. As shown in FIGS. 7 and 8, at least one valve, mass flow controller, indicator, sensor, and the like may be positioned on or in communication with the mixed gas conduit 132. For example, two (2) valves 134 and one (1) indicator 136 are included on the embodiment of the ozonated water delivery system 100 shown in FIGS. 7 and 8 configured to prevent the backflow of water and/or gas into the gas source 130, although those skilled in the art will appreciate that any number or valves, mass flow controllers, indicators, sensors, and the like may be coupled to or in communication with the mixed gas conduit 132.

During use, the aqueous carbon dioxide solution is introduced into the first contacting device 102a via the solution conduit 120. In addition, the mixed gas from the mixed gas conduit 132 is introduced into the second contacting device 102b. Some mixed gas is directed from the second contacting device 102b to the first contacting device 102a via at least one off gas coupling conduit 164 which is in fluid communication with the first contacting device 102a and the second contacting device 102b. The mixed gas from the second contacting device 102b may be introduced into the first contacting device 102a and reacts with the aqueous carbon dioxide within the first contacting device 102a thereby dissolving the ozone within the mixed gas in the aqueous carbon dioxide solution to provide a dissolved ozone/UPW solution. The dissolved ozone/UPW solution within the first contacting device 102a may be removed from the first contacting device 102a via at least one first contacting device conduit 152 and flowed into the second contacting device 102b, while off gas 166 is removed from the first contacting device 102a via at least one first contacting device off gas conduit 168. In the illustrated embodiment at least one pump 150 may be used to direct the dissolved ozone/UPW solution from the first contacting device 102a to the second contacting device 102b via the first contacting device conduit 152.

Referring again to FIGS. 8 and 9, the dissolved ozone/UPW solution from the first contacting device 102a is directed into the second contacting device 102b in the presence of the mixed gas from the gas source 130. As a result, the ozone the mixed gas within the second contacting device 102b dissolves in the dissolved ozone/UPW solution thereby resulting in higher concentration of dissolved ozone 160 which may be outputted from the second contacting device 102b via at least one second contacting device output conduit 162. Those skilled in the art will appreciate that although FIGS. 7 and 8 show the first and second contacting devices coupled in series, the first and second contacting devices may be coupled in any desired configuration.

Optionally, FIG. 9 shows an alternate embodiment of the ozonated water delivery system 100 shown in FIG. 8 having at least one processor therein. Like the previous embodiments described above, at least one sensor, indicator, valve or the like may be positioned on the second contacting device output conduit 162. For example, in the illustrated embodiment, a sensor 170 is coupled to the second contacting device output conduit 162 although those skilled in the art any variety of other components, such as pressure sensors or level sensors, may similarly be included. The sensor 170 may be in communication with at least one processor 174 via at least one processor conduit 172. Further, the processor 174 may be in communication with at least one of the UPW source 104, mass flow controller 114, indicator 116, gas source 130, mass flow controller 134, pump 150, and indicator 136 via the processor conduit 172. As such, the processor 174 may be configured to receive data from and provide data to at least one of the UPW source 104, mass flow controller 114, indicator 116, gas source 130, mass flow controller 134, indicator 136, and sensor 170. During use, the processor 174 may be configured to monitor the dissolved ozone concentration, and similar characteristics of the ozonated water and selectively vary the performance of the UPW source 104, mass flow controller 114, indicator 116, gas source 130, mass flow controller 134, pump 150, and sensor 170 accordingly. The pump 150 may be controlled to set the pressure of contacting device 102b 0.1 bar to 1 bar higher than the contacting device 102a, such as 0.2 bar to 0.7 bar higher, although those skilled in the art will appreciate that the contacting device 102b may operate at any desire pressure. As such, although not shown in FIG. 9, those skilled in the art will appreciate that the pump 150 may be in communication with the processor 174. The pressure in the second contacting device 102b will be controlled by the processor 174 to an effectively constant value. The pressure of the second contacting device 102b can be configured to be between 1 bar and 4 bar, such as between 1.8 bar and 2.5 bar.

The embodiments disclosed herein are illustrative of the principles of the invention. Other modifications may be employed which are within the scope of the invention. Accordingly, the devices disclosed in the present application are not limited to that precisely as shown and described herein.

What is claimed:

1. An ozonated water delivery system, comprising:
a first contacting device;
at least one ultrapure water source configured to provide ultrapure water to the first contacting device;
at least one ultrapure water conduit coupled to the at least one ultrapure water source and the first contacting device;
at least one gas source providing at least one gas forming at least one solution when reacted with the ultrapure water;
at least one gas conduit in communication with the at least one gas source and at least one of the at least one ultrapure water source and the at least one ultrapure water conduit;
at least one solution conduit in communication with the first contacting device and the at least one ultrapure water source, the at least one solution conduit configured to receive the at least one solution and deliver the at least one solution to the first contacting device;
at least a second contacting device in communication with the first contacting device via at least one first contacting device conduit;
the at least one first contacting device conduit configured to transport ozonated water outputted from the first contacting device to the at least a second contacting device;
at least one mixed gas conduit in communication with the at least one gas source and the at least a second contacting device, the at least one mixed gas conduit configured to provide at least one mixed gas to the at least a second contacting device;
at least one off gas conduit in communication with the at least a second contacting device and the first contacting device, the at least one off gas conduit configured to direct a portion of the at least one mixed gas from the at least a second contacting device to the first contacting device; and
at least one ozonated water output conduit in communication with the at least a second contacting device.

2. The ozonated water delivery system of claim 1, wherein the at least one of the first contacting device and the at least a second contacting device comprises at least one packed column contacting device.

3. The ozonated water delivery system of claim 1, wherein the at least one of the first contacting device and the at least a second contacting device comprises at least one pack column contacting device including tower packing therein.

4. The ozonated water delivery system of claim 1, wherein the at least one of the first contacting device and the at least a second contacting device comprises at least one membrane-based contacting device having at least one membrane module therein.

5. The ozonated water delivery system of claim 1, further comprising at least one pump in communication with the first contacting device and the at least a second contacting device, the at least one pump configured to pump ozonated water outputted from the first contacting device to the at least a second contacting device.

6. The ozonated water delivery system of claim 1, wherein the at least one gas source is configured to provide carbon dioxide to at least one of the at least one ultrapure water source, the at least one ultrapure water conduit, and the at least one solution conduit, thereby forming an aqueous carbon dioxide solution.

7. The ozonated water delivery system of claim 6, wherein the at least one gas source is configured to flow carbon dioxide to at least one ultrapure water source, the at least one ultrapure water conduit, and the at least one solution conduit at a flow rate of about 0.01 SLPM to about 0.5 SLPM.

8. The ozonated water delivery system of claim 1, wherein at least one mixed gas flowing from the at least one gas source to the at least a second contacting device via the at least one mixed gas conduit is comprised of oxygen, ozone, and carbon dioxide.

9. The ozonated water delivery system of claim 1, wherein at least one mixed gas flowing from the at least one gas source to the at least a second contacting device via the at least one mixed gas conduit may include at least one gas selected from the group nitrogen, nitrogen dioxide, and dinitrogen dioxide.

10. The ozonated water delivery system of claim 1, further comprising at least one of a processor, valve, mass flow controller, flow sensor, gauge, indicator, flow restrictor, pump, and sensor positioned on at least one of the at least one gas source, at least one ultrapure water source, at least one ultrapure water conduit, at least one solution conduit, a least one first contacting device conduit, at least one mixed gas conduit, at least one off gas conduit, and at least ozonated water outlet conduit.

* * * * *